Figure 1:
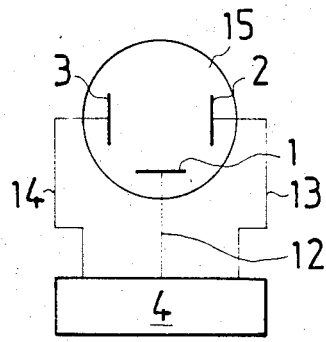

United States Patent [19]

Moilanen et al.

[11] Patent Number: 4,605,900
[45] Date of Patent: Aug. 12, 1986

[54] ELECTRODE SYSTEM FOR VOLTAMETRIC MEASUREMENTS

[75] Inventors: Juhani Moilanen; Markku Pietikäinen, both of Kajaani, Finland

[73] Assignee: Kajaani OY, Finland

[21] Appl. No.: 493,459

[22] Filed: May 11, 1983

[30] Foreign Application Priority Data

May 12, 1982 [FI] Finland ................................. 821670

[51] Int. Cl.⁴ ............................................ G01N 27/00
[52] U.S. Cl. ................................ 324/439; 324/450; 204/400; 204/412
[58] Field of Search ................ 324/438, 439, 446–450; 204/404, 412, 400, 1 B, 1 C, 406

[56] References Cited

U.S. PATENT DOCUMENTS 3,692,624  9/1972  Yrjala ..................................... 162/49
3,919,067  11/1975  Carson, Jr. et al. ................ 204/412
4,040,931  8/1977  Wilson ................................. 204/404
4,326,927  4/1982  Stetter et al. ...................... 204/406

Primary Examiner—Reinhard J. Eisenzopf
Assistant Examiner—Kevin D. O'Shea
Attorney, Agent, or Firm—Darby & Darby

[57] ABSTRACT

An electrode system for voltametric measurements for measuring oxidative and reductive compounds in aqueous solutions primarily in the paper and pulp industries, said system comprising a working electrode (1), a counter-electrode (2) and a reference electrode (3), these being connected to a voltametric measuring apparatus (4). The aim is to introduce an electrode system mountable in the process pipeline with greater ease than electrodes of prior art and of a construction simpler than earlier systems, and more durable and less maintenance-requiring than these.

As taught by the invention, the reference electrode (3) is a metal electrode and has been made for instance of silver, platinum, gold, titanium or "Hastalloy C" steel. The electrodes are advantageously installed together and in one and the same pick-up and disposed to be so placed in the process pipe system that the solution flowing in the pipe system flushes the electrodes.

10 Claims, 9 Drawing Figures

ELECTRODE SYSTEM FOR VOLTAMETRIC MEASUREMENTS

The present invention concerns an electrode system for voltametric measurements as has been defined in the introductory part of claim 1.

Normally, in voltametric measurements are used three electrodes: a working electrode, a counter-electrode and a reference electrode. The electrodes are inserted in a measurement cell, that is, in the solution that is being measured. By using the measurement equipment, that is, the electronic part of the measurement apparatus, a constant potential difference is adjusted to be present between the working and reference electrodes connected to the measurement equipemnt, this difference being selected in the so-called limit current range of the substance being measured, whereby the oxidation or respectively the reduction of the substance on the surface of the working electrode is adjusted to be faster than the transport of the substance thereto. This implies that the content of the compound being analyzed is zero on the surface of the working electrode. The transport of the compound to be analyzed to the surface of the working electrode may be so arranged that the sample flows past the working electrode, or alternatively, the working electrode is moved in relation to the sample e.g. by rotating it.

Owing to the influence of the electron transfer reaction (oxidation or reduction of the compound being measured) taking place on the surface of the working electrode, the potential difference between the working and reference electrodes tends to change. The change is observed by the aid of the electronic part of the measuring equipment, and it is prevented by supplying a current to the working electrode through the counter-electrode. The electric current thus produced is directly proportional to the percentage of the compound being analyzed, on the basis of the relationship that the greater the number of electron transfer reactions taking place, the greater is the intensity of the current suppied by the electronic part through the counter-electrode to the working electrode.

In continuous-operation analytic measurement, the reference electrode is the weakest point in the system. The working and counter-electrodes are as a rule metal electrodes and therefore durable and requiring less maintenance. In systems known in the art, the reference electrode is connected to the sample solution either by a capillary or by a sinter and a salt bridge or another equivalent system, whereby the quality and purity of the sample determine the service life of this kind of connection. In all events, the service life of the reference electrode is remarkably shorter than that of the working and counter-electrodes.

Also the pressure variations in the sample cause problems in the reference electrode. The changes of pressure may block or interrupt the salt bridge of the reference electrode, whereby the potential of the work electrode changes and causes an error in the measurement.

Furthermore, the installation of previously known reference electrodes in the process pipe system is highly inconvenient, because the reference electrodes are usually of great size and/or easily breakable. In addition, the sealing of the installation of a reference electrode is difficult, because the reference electrodes tolerate poorly mechanical stresses.

In connection with the installation of voltametric measurement devices or prior art, a separate sample line branching from the actual process line is generally used. This is often a complex, time-consuming and costly design solution. Furthermore, the sample lines may be blocked time and again, and this detracts from the reliability of process control on the basis of the measurements.

Furthermore, in connection with voltametric measurements an installation procedure (disclosed in Finnish Pat. No. 42,766, corresponding to U.S. Pat. No. 3,692,624) is used wherein e.g. from the pulp slurry is taken a separate filtration sample by means of separate sampling equipment, and from which a sample is conducted to the measurement cell to be analyzed. In this case, objectionable soiling of the working and counter-electrodes is incurred in the pick-up, giving rise to measurement errors.

The object of the present invention is to eliminate the drawbacks presented in the foregoing and to provide an electrode system in connection of which no drawbacks as mentioned above occur. The object of the invention is specifically to provide an electrode system and a pick-up design in particular for measurements of bleaching chemicals content in the cellulose industry for placement directly in the production line, in a pipe or column, to measure the bleaching chemicals, to be used specifically in connection with the dispensing and controlling of said chemicals.

Regarding the characteristic features of the invention, reference is made to the claims.

The present invention is based on the feature that the reference electrode, as well as the working and counter electrodes, are made of metal. The reference electrode is advantageously made of an inert metal, such as platinum, silver, gold, titanium, Hastalloy C (a nickel-molybdenum alloyed steel), etc., or of an alloy of such. All the electrodes, the reference electrodes as well as the working and counter-electrodes, are preferably installed in one and the same pick-up, advantageously in the end of a rod-shaped pick-up directly pushable into the process pipe system.

The electrode system of the invention is substantially simpler and more durable and needs less maintenance than the electrode systems of prior art used in voltametric measurements. The electrode sysytem tolerates variations of pressure, mechanical stresses, and when the electrodes are in direct contact with the process solution, as with pulp slurry for instance, the electrodes are continuously flushed with the process solution and, therefore, remain unsoiled and chemically unchanged. The electrode system is substantially easier to mount in the pipe system than those of prior art.

The electrode system of the invention therefore eliminates the drawbacks mentioned above, occurring in prior art. Furthermore, the electrode system of the invention meets the structural, operational and strength requirements imposed on electrode systems for voltametric measurements intended to work in severe conditions, in particular in the paper and pulp industry.

In the electrode system of the invention, the shape of the electrode may be e.g. round, rod-shaped, annular or any other shape, or a combination of these. In the electrochemical sense, the operation of an electrode system of this type, intended for voltametric measurements, is substantially fully equivalent with altogether conventional voltametric electrode systems known in the art. Nevertheless, depending on the material of the reference electrode, the so-called limit current range occurring in the potential between the working and reference electrodes may lie in another potential range. This is due to the fact that different metals or alloys possess a different oxidation/reduction potential e.g. in relation to hydrogen ($H_2$). Based on this difference, the material of the reference electrode can be selected to be suitable for analyzing the concentration of another compound or other compounds. It is then possible, since the solution that is being analyzed contains either a reductive or oxidative compound (e.g. in cellulose bleaching, acidifying of the $ClO_2$ radical with $SO_2$), to select the structure of the reference electrode so that at a given potential between the working and reference electrodes one compound is reduced (for instance $ClO_2$) and the other is oxidized (for instance $SO_2$), whereby it is possible by the analysis to determine which of the two compounds is present in the solution and what is its content (selective analysis).

Figure 2:
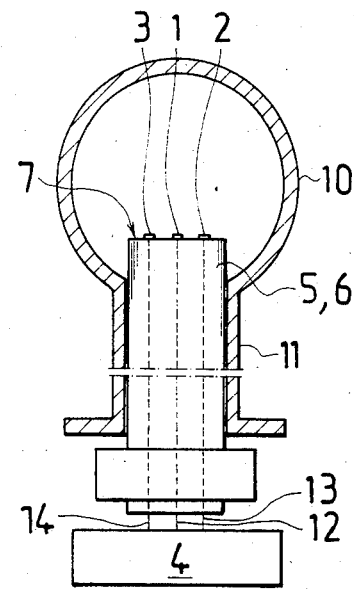
Figure 3:
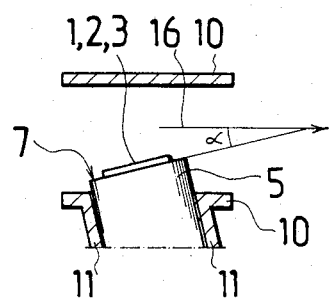
Figure 4:
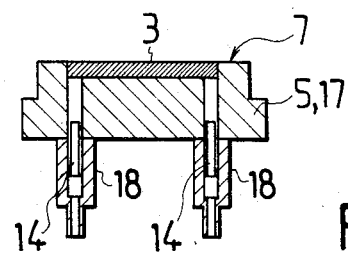
Figure 5:
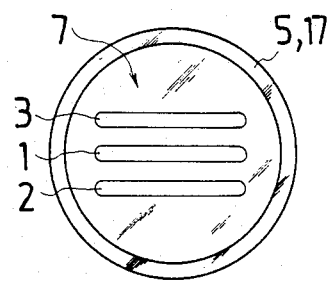
Figure 6:
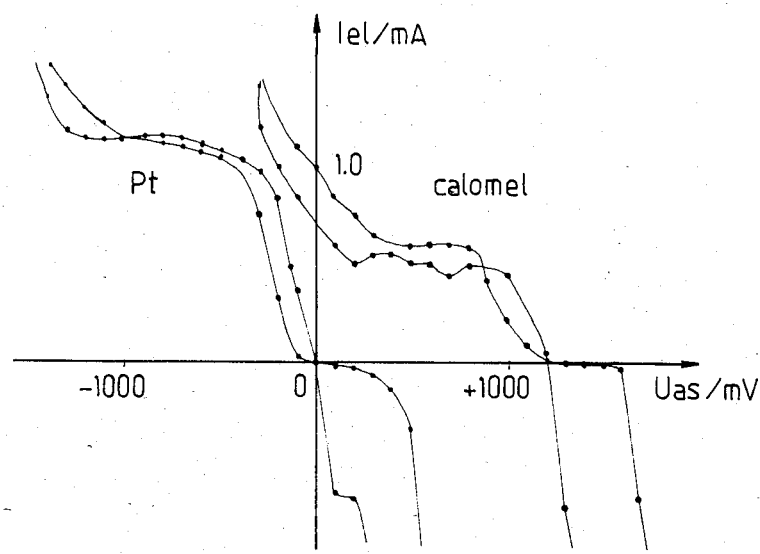
Figure 7:
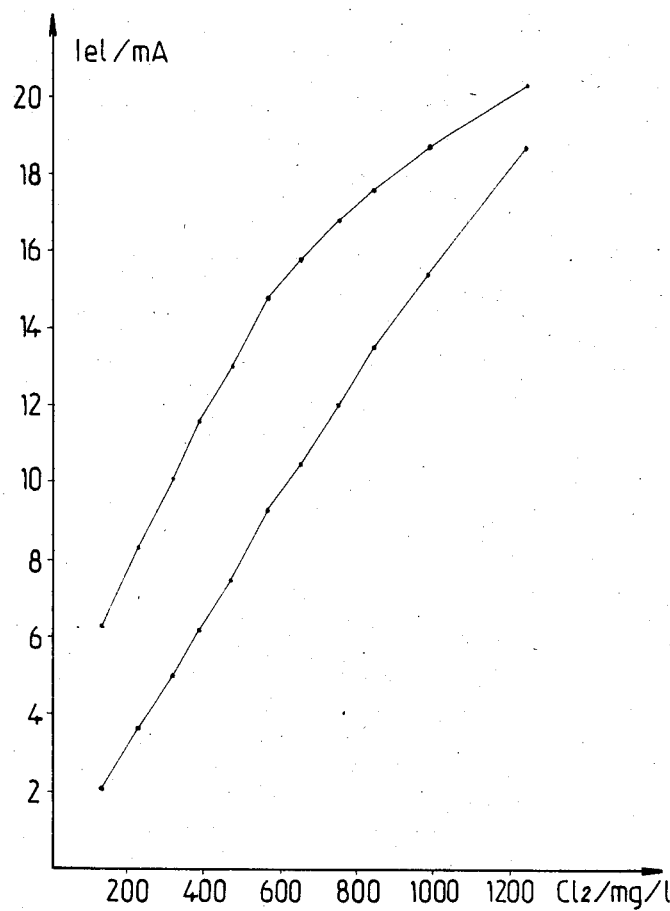
Figure 8:
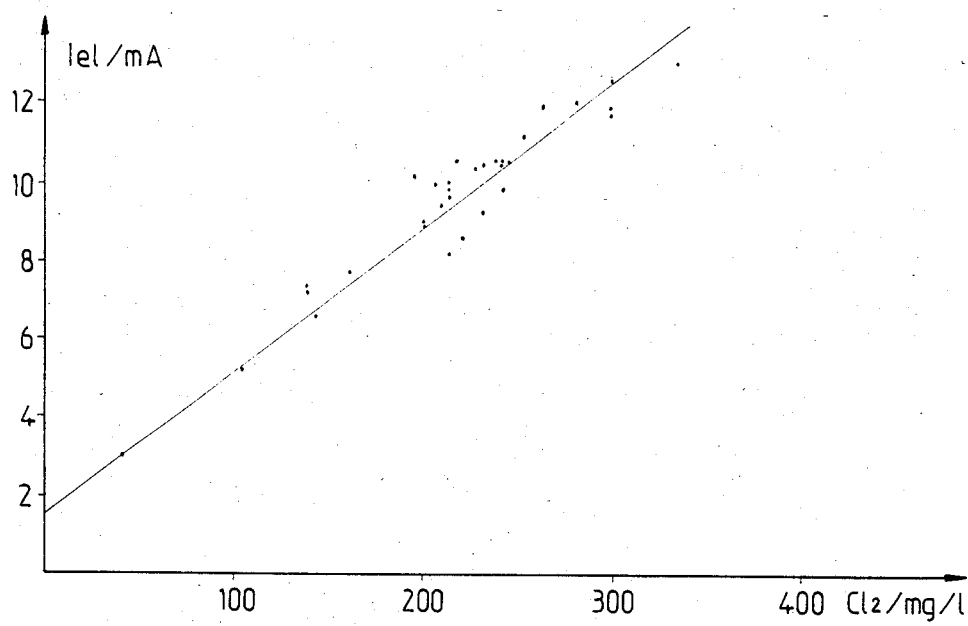
Figure 9:
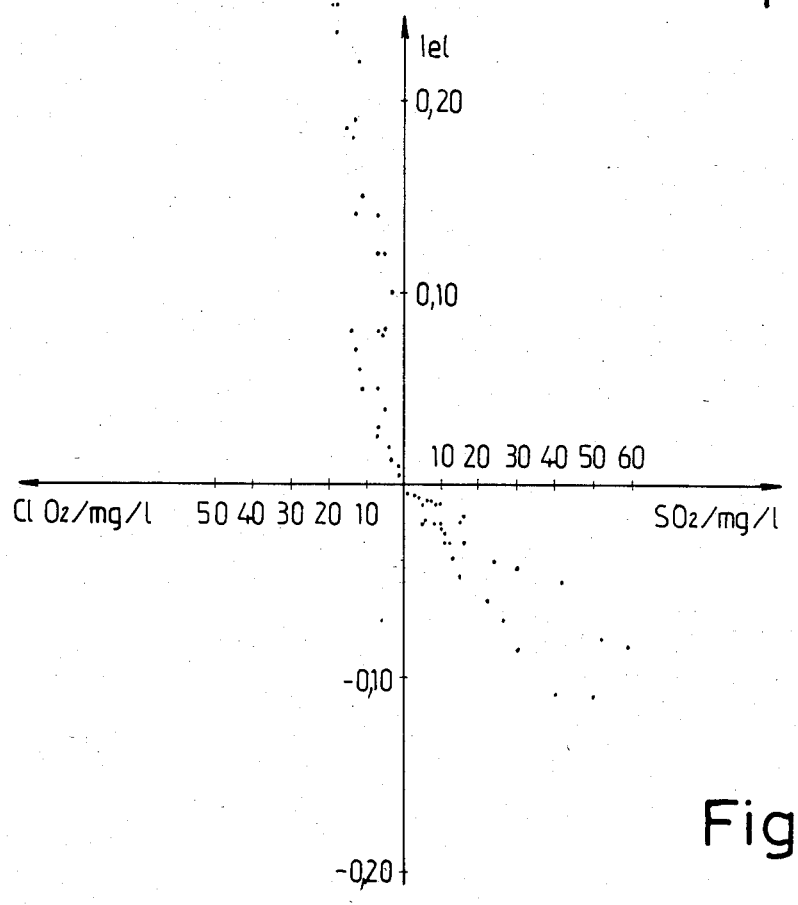

The invention is described in the following in detail with the aid of embodiment examples, reference being made to the drawings attached, wherein:

FIG. 1 presents in a schematic diagram the circuit connection of the electrode system used in voltametric measurements, FIG. 2 presents a pick-up provided with an electrode system according to the invention, the pick-up being inserted in a process pipe, transversely sectioned, FIG. 3 presents another pick-up provided with an electrode system according to the invention and placed in a process pipe, sectioned longitudinally to the process pipe, FIG. 4 presents the end of a third pick-up provided with an electrode system according to the invention, in elevational view and sectioned, FIG. 5 shows the same pick-up as FIG. 4, in the end view, FIG. 6 presents graphically the test results obtained in some voltametric measurements with a conventional calomel reference electrode and with a metallic reference electrode according to the invention, the electrode currents being functions of the potential difference between the working and reference electrodes, FIG. 7 shows graphically results of measurement obtained with a calomel reference electrode and with a metallic reference electrode according to the invention, the electrode currents being plotted for constant potential difference between the working and reference electrodes, as a function of chlorine content, FIG. 8 shows graphically results of measurement from an in-process test using a metallic reference electrode according to the invention and interdependence of electrode current and chlorine content, and FIG. 9 shows graphically the test results from another in-process test for determining chlorine dioxide and sulphur dioxide in the pulp slurry in a chlorine dioxide bleaching process.

FIG. 1 shows the circuit diagram of a conventional system, and at the same time that of the present invention, of three electrodes for voltametric measurements. The system comprises a working electrode 1, a counter-electrode 2 and a reference electrode 3 placed in a measuring cell 15, e.g. in a process pipe, containing the solution to be analyzed. The electrodes 1, 2, 3 have been connected by leads 12, 13 and 14, respectively, with the measuring apparatus 4, that is, with the electronic part. The electronic part has been arranged to supply and control a constant potential difference between the working and reference electrodes 1 and 2, this being selected to lie in the so-called limit current range of the substance being measured. Thus, the oxidation or reduction of the substance under measurement has been adjusted to be faster on the surface of the working electrode than the transport of the substance to this surface. Thereby, the concentration of the compound being analyzed is zero on the surface of the working electrode. The arrangement is conventional and has been described for instance in the same applicant's earlier Finnish Pat. No. 42766 corresponding to U.S. Pat. No. 3,692,624.

In the embodiment of FIG. 1, all electrodes—the working electrode 1, the counter-electrode 2 and the reference electrode 3—are metal electrodes, e.g. of platinum as taught by the invention.

In FIG. 2 is seen an embodiment wherein the working electrode 1, the counter-electrode 2 and the reference electrode 3 have been mounted in one and the same pick-up. The pick-up 5 is rod-shaped and is inserted into a process pipe 10 through a closure 11, i.e., a sealing pipe. The end 7 of the pick-up 5 is substantially planar and constitutes a surface in contact with the pulp slurry being measured and circulating in the pipes 10. The electrodes 1, 2, 3 are rod-shaped, and they are disposed on said end face of the pick-up substantially paralleling the flow direction of the solution in the pipe system, with the working electrode in the centre. The electrodes 1, 2, 3 are each connected with leads 12, 13 and 14, respectively, to the electronic part 4 of the measuring apparatus as shown in FIG. 1 and presented in the foregoing. The rod-shaped pick-up 5 is made e.g. of PVC or PVDF plastics or of titanium.

The pick-up shown in FIG. 3 is substantially similar to the pick-up shown in FIG. 2, with electrodes 1, 2, 3. In FIG. 3, as in FIG. 2, the pick-up 5 comprises a frame part 6 in contact with the aqueous solution flowing in the pipe line 10 an which has been made of a suitable insulating material. The electrodes 1, 2, 3 project in part to the surface 7 of the frame part in contact with the solution being measured. The electrodes have been fixedly installed in the pick-up 5 and advantageously in the manner that the solution flowing in the pipes flushes the electrodes. In FIG. 3, the surface 7 of the frame part 6 of the pick-up 5 in contact with the flowing solution, with the electrodes mounted thereon, subtends a substantially acute angle $a$ with the direction of flow of the solution flowing in the pipes. Thereby, the flowing solution, such as pulp slurry for instance, continuously keeps the electrodes clean.

In FIGS. 4 and 5 is shown the end part 17 of a third pick-up according to the invention, with electrodes. The end part 17 is composed of flange-like, circular member in the face 7 of which the electrodes 1, 2, 3 have been so countersunk that they protrude onto said surface. The electrodes have rod shape an they have been inserted in parallel, side by side and with equal spacing in the surface of the end part, with the working electrode in the center. The end part is provided with connecting pins 18 and leads 14 for each electrode 1, 2, 3, for pushing on the end of the pick-up, with the pins entering corresponding plug sockets on the pick-up (the pick-up not depicted in FIGS. 4 and 5.).

If desired, the electrodes may be mounted not only on the end of the pick-up but equally on its sides. The spacing of the electrodes is suitably less than 10 mm, whereby e.g. the variations in conductivity of the compounds being analysed, in connection with bleaching, will not interfere with the measurements. The electrode system may be symmetrical or asymmetrical. If the electrode system is not symmetrical, that electrode is selected to be the working electrode which lies closest both to the counter-electrode and to the reference electrode.

In the following are presented the test results obtained with a reference electrode of metal or made of a metal alloy, juxtaposed with those obtained with a calomel electrode. In the experimental measurements were used the electrode and the pick-up arrangement of FIG. 2, the pick-up mounted at 30° against the sample flow. In the reference tests, working and counter-electrodes of platinum with radius 5 mm were used on the side of a calomel electrode. In all tests, the electrodes were connected as in FIG. 1 to a "POLAROX" analyser; thus, the electronic part 4 of the electrode systems was exactly the same in all tests.

The laboratory tests were carried out with apparatus accommodating about 25 liters of the sample, the sample bing circulated in the pipe system by the aid of a pump.

The plant-scale tests were carried out in connection with fullsize factory processes.

EXAMPLE 1

The pH of the solution used in the measurement was adjusted with hydrochlorid acid 1 to 2.0, whereafter water containing chlorine was added to the water to bring the chlorine content up to 80 mg per liter. The chloride content was analyzed by iodometric titration. The temperature of the sample was about 20° C. In the measurement, the potential between the working and reference electrodes in both electrode systems (=set point potential, $U_{as}$, mV) was manually changed in steps of 100 mV in the range $-2000$ mV ... $+2000$ mV. Simultaneously, the currents passing in the measurement circuits corresponding to each set potential (=electrode currents, $I_{el}$, mA) were measured: The results are presented graphically in FIG. 6.

FIG. 6 clearly reveals the so-called limit current range in which the electrode current is nearly constant independent of the set potential: for calomel electrodes about $+220$ mV ... $+800$ mV, for a platinum electrode $-1200$ mV ... $-400$ mV. In addition, the graphs reveal that the limit current range lies at different set point potentials for different reference electrodes. The shift of the limit current range, as well as that of the electrode current zero point, is due to the material of the reference electrode.

EXAMPLE 2

The solution being measured was water, its pH adjusted with hydrochloric acid to be 2.2. In the test, chlorine was added to the water portions. After each addition the electrode current in both electrode systems was measured and the chlorine content of the solution was analyzed by iodometric titration. For the working, counter and reference electrodes in the electrode system of the invention was used platinum rod material, the pick-up being as shown in FIG. 2. The pick-up was so inserted in the sample flow that the sample proceeded parallel to the longitudinal axes of the electrodes. The potential of the working and reference electrodes in the electrode system according to the invention was adjusted to be $-1100$ mV and that between the working and reference electrodes in the electrode system serving as reference was adjusted to be $+200$ mV. The results are seen in FIG. 7, the results obtained with the electrode system of the invention lower down and the results produced by the calomel reference electrode with platinum working and counter-electrodes higher up.

The test results reveal that the electrode current from the electrode system according to the invention is more closely linear for chlorine than that of the electrode system serving as reference.

EXAMPLE 3

The measurements were carried out at the chlorination step of the bleaching in a sulphate pulp mill, using the same electrode system as in Example 2. The measurements were made directly from the process from among the pulp slurry, in which changes of chlorine content were induced. At the same time, samples were taken from the point of measurement and their chlorine content was determined by titration. In the measurements, the corresponding electrode current intensities were determined ($I_{el}$, mA). The pH value varied during the measurements from 1.8 to 2.0, the temperature from 22 to 27° C., $U_{as}$ was $-11$ mV. The results of measurement are presented graphically in FIG. 8.

During the test period of four days, the stability of the electrode system was good. The reference electrode was a platinum electrode.

EXAMPLE 4

The measurements were carried out in the chlorine dioxide step of the bleaching process in a sulphate cellulose mill, using the electrode system of FIG. 2. The measurements were made directly from among the pulp slurry containing chlorine dioxide or sulphur dioxide, in other words a reductive/oxidative pair of compounds. For the reference electrode was used a silver electrode; the working and counter-electrode were of platinum, whereby at a certain potential between the working and reference electrodes $U_{as}= +400$ mV) the chlorine dioxide is reduced and the sulphur dioxide is oxidized on the working electrode. The reduction of chlorine dioxide produces an electrode current with the $+$ sign and the oxidation of sulphur dioxide produces an electrode current with the $-$ sign, whereby with the electrode system it is possible to analyze whether the process contains chloride dioxide or sulphur dioxide, and what is the content. Such analysis is not feasible if for reference electrode is used e.g. platinum, because with any potential between the working and reference electrodes the chlorine dioxide and sulphur dioxide both give rise to an eletrode current with the same sign, that is, both are either reduced or oxidized, and therefore the analysis cannot tell which of the two compounds is present in the solution under measurement.

The results of measurement are presented graphically in FIG. 9.

The embodiment examples are intended for illustration of the invention without confining it in any way.

I claim:

1. An electrode system for voltametric measurements of oxidative and reductive compounds in aqueous solutions, comprising:
    a working electrode,
    a counter-electrode,
    a reference electrode, and
    a single pick-up, each of said three electrodes being mounted in said pick-up,
    each of said electrodes being connected to a voltametric measuring apparatus, said reference electrode being a metal electrode, wherein a constant voltage is maintained between said reference and working electrodes by said voltametric measuring apparatus, wherein said pick-up further comprises a frame part in contact with the aqueous solution being measured, said frame part made of insulating material, said electrodes at least partly projecting through the surface of the frame part so as to be in contact with the solution being measured.

2. An electrode system according to claim 1, wherein the reference electrode is made of a metal selected from the group: silver, platinum, gold, titanium, and Hastalloy C (a nickel-molybdenum alloyed steel).

3. An electrode system for voltametric measurements of oxidative and reductive compounds in aqueous solutions, comprising:

a working electrode, a counter-electrode, a reference electrode, and a single pick-up, each of said three electrodes being mounted in said pick-up, each pf said electrodes being connected to a voltametric measuring apparatus, said reference electrode being a metal electrode, wherein a constant voltage is maintained between said reference and working electrodes by said voltametric measuring apparatus, and wherein the electrodes are fixedly mounted on the pick-up.

4. An electrode system according to claim 3, wherein the electrodes are fitted in a process pipe system so that the aqueous solution flowing in the pipe system flushes the electrodes.

5. An electrode system according to claim 3, wherein a surface of the frame part of the pick-up in contact with the solution being measured subtends a substantially acute angle with the directin of flow of the solution flowing in the pipe system.

6. An electrode system according to claim 5, wherein the pick-up is rod-shaped and is inserted into the process pipe system through a closure device, the end of the pick-up is substantially planar constituting a surface in contact with the solution being measured, and the electrodes are rod-shaped and placed on said surface substantially paralleling the direction of flow of the solution flowing in the pipe system, with the working electrode in the center.

7. An electrode system according to claim 3, wherein the reference electrode is made of a metal selected from the group: silver, platinum, gold, titanium, and Hastalloy C (a nickel-molybdenum alloyed steel).

8. An electrode system according to claim 7, wherein the electrodes are fitted in a process pipe system so that the aqueous solution flowing in the pipe system flushes the electrodes.

9. An electrode according to claim 7, wherein a surface of the frame part of the pick-up in contact with the solution being measured subtends a substantially acute angle with the direction of flow of the solution flowing in the pipe system.

10. An electrode system according to claim 9, wherein the pick-up is rod-shaped and is inserted into the process pipe system through a closure, the end of the pick up is substantially planar constituting a surface in contact with the solution being measured, and the electrodes are rod-shaped and placed on said surface substantially paralleling the direction of flow of the solution flowing in the pipe system, with the working electrode in the center.

* * * * *